United States Patent [19]

Longman et al.

[11] Patent Number: 5,094,818
[45] Date of Patent: Mar. 10, 1992

[54] SELF-FILLING ANTI-SIPHON FLOW SYSTEM FOR PARTICLE ANALYSIS

[75] Inventors: Millard Longman, Tamarac; Oscar Proni, Hollywood; Richard A. Burdman, Miami, all of Fla.

[73] Assignee: Exact Science, Inc., Miami, Fla.

[21] Appl. No.: 347,522

[22] Filed: May 4, 1989

[51] Int. Cl.$^5$ .................................. G01N 33/00
[52] U.S. Cl. .................................. 422/73; 324/71.4; 422/81; 422/82.01
[58] Field of Search .............. 324/71.4; 422/73, 81, 422/82.01

[56] References Cited

U.S. PATENT DOCUMENTS

| | | | |
|---|---|---|---|
| 3,299,354 | 1/1967 | Hogg | 324/71 |
| 3,444,463 | 5/1969 | Coulter | 324/71 |
| 3,648,158 | 3/1972 | Parker | 324/30 B |
| 3,746,976 | 7/1973 | Hogg | 324/71 CP |
| 3,781,675 | 12/1973 | Angel | 324/71 CP |
| 3,793,587 | 2/1974 | Thom et al. | 324/71 CP |
| 3,854,088 | 12/1974 | Gahwiler | 324/71 CP |
| 3,902,115 | 8/1975 | Hogg et al. | 324/71 CP |
| 3,924,180 | 12/1975 | Salzman et al. | 324/71.4 |
| 3,930,736 | 1/1976 | Coulter | 324/71.4 |
| 4,157,499 | 6/1979 | Kacerek | 324/71 CP |
| 4,564,803 | 1/1986 | Loren et al. | 324/71.1 |
| 4,631,483 | 12/1986 | Proni et al. | 324/71.4 |
| 4,653,078 | 3/1987 | Aritomi et al. | 324/71.4 |
| 4,710,021 | 12/1987 | Von Behrens | 324/71.4 |
| 4,767,600 | 8/1988 | Vicario | 422/73 |

Primary Examiner—Peter Chin
Attorney, Agent, or Firm—Richard D. Schmidt

[57] ABSTRACT

A fluid flow system for use with an analytical instrument is provided having a sample reservoir for holding a liquid suspension of particles to be analyzed, a reagent reservoir for holding a reagent, pump means for pumping fluid to and from the reservoirs to a pumping reservoir, valve means for restricting fluid flow from the reagent reservoir to the pumping reservoir, first conduit means interconnecting the reagent and sample reservoirs, second conduit means connecting the sample and pumping reservoir at a point just behind a metered aperture provided in an end of the second conduit means, and in a preferred embodiment, third conduit means connecting the first and second reservoirs and valve means for restricting fluid flow from the reagent reservoir to the pumping reservoir through the third conduit means, the end of each of the conduit means being maintained at the same physical level.

26 Claims, 8 Drawing Sheets

SELF-FILLING ANTI-SIPHON FLOW SYSTEM FOR PARTICLE ANALYSIS

The present invention relates to an apparatus and method for effecting liquid flow in an analytical instrument and in particular to those instruments used to analyze biological or industrial samples.

BACKGROUND OF THE INVENTION

Analysis of liquid samples typically involves aspiration of liquid from the sample through a conduit having a metered aperture at its immersed end. The typical particle analyzer consists of three components: a sample vessel, a liquid flow system, and a sensor.

Particle analyzers move suspended biological or industrial particles from the sample vessel to the sensor, via the liquid system. The sensor detects, counts, and identifies the particles. The liquid flow system then moves the sample into a waste container.

Detecting, counting and identifying particles can be done by a variety of sensors. These include impedance, light scatter, and fluorescence type sensors. Regardless of which sensing mechanism is used, the analyzer also needs a liquid flow system.

Many instruments need prepared samples for analysis. The preparation may be as simple as mixing the sample with a reagent. Usually, sample preparation is a two step process. First, the sample is collected in a suitable vessel and then it is prepared by diluting it in salt water. After the analytical cycle is complete, a valve must be closed to prevent draining of the diluent supply from the system by siphon action before new liquid samples are situated for analysis. Conventional liquid flow systems use a combination of pinch valves and/or stopcocks to accomplish this task. These methods are deficient because stopcocks must be manually operated, while normally-closed pinch valves have a tendency to cause a permanent deformation of the system tubing. In addition, most liquid systems for analytical instruments use stepper motors or peristaltic pumps, timing controls, and diluting assemblies. These precision liquid systems are expensive, complex, and require periodic maintenance for reliable operation. This is especially true of systems used to analyze microscopic particles such as red and white blood cells.

In addition, the current design of most particle collection and dilution assemblies have deficiencies in their design and operation which reduce the accuracy and efficiency of their measurements and the complexity of maintenance. Collectively, these features decrease the efficiency and drastically increase the cost of operation of such analytical instruments. There exists, therefore, a need for a simple yet reliable liquid control system which overcomes these deficiencies by eliminating the pinch valves and manually operated stopcocks yet provides for reliable, low maintenance operation.

It is an object of the present invention to provide a self-filling, anti-siphon liquid flow system devoid of pinch valves or manually operated stopcocks and which is simple to operate and maintain.

It is an additional object of this invention to provide an analytical instrument for detecting, counting and identifying particles which has multiple liquid flow sub-systems to aspirate samples from multiple sample containers and which may have multiple analytical channels.

SUMMARY OF THE INVENTION

These and other objects are achieved by a fluid flow system for use with an analytical instrument having a sample reservoir for holding a liquid suspension of particles to be analyzed, a reagent reservoir for holding a reagent, pump means for pumping liquid to and from the reservoirs to a pumping reservoir, valve means for restricting fluid flow from the reagent reservoir to the pumping reservoir, first conduit means interconnecting the reagent and sample reservoirs, second conduit means connecting the sample and pumping reservoir at a point just behind a metered aperture provided in an end of the second conduit means, and in a preferred embodiment, third conduit means connecting the first and second reservoirs and valve means for restricting fluid flow from the reagent reservoir to the pumping reservoir through the third conduit means, the end of each of the conduit means being maintained at the same physical level.

BRIEF DESCRIPTION OF THE DRAWINGS

In the following description of the preferred embodiment of the invention, reference is had to the accompanying drawings, in which.

DETAILED DESCRIPTION OF THE PREFERRED EMBODIMENT

Figure 1:
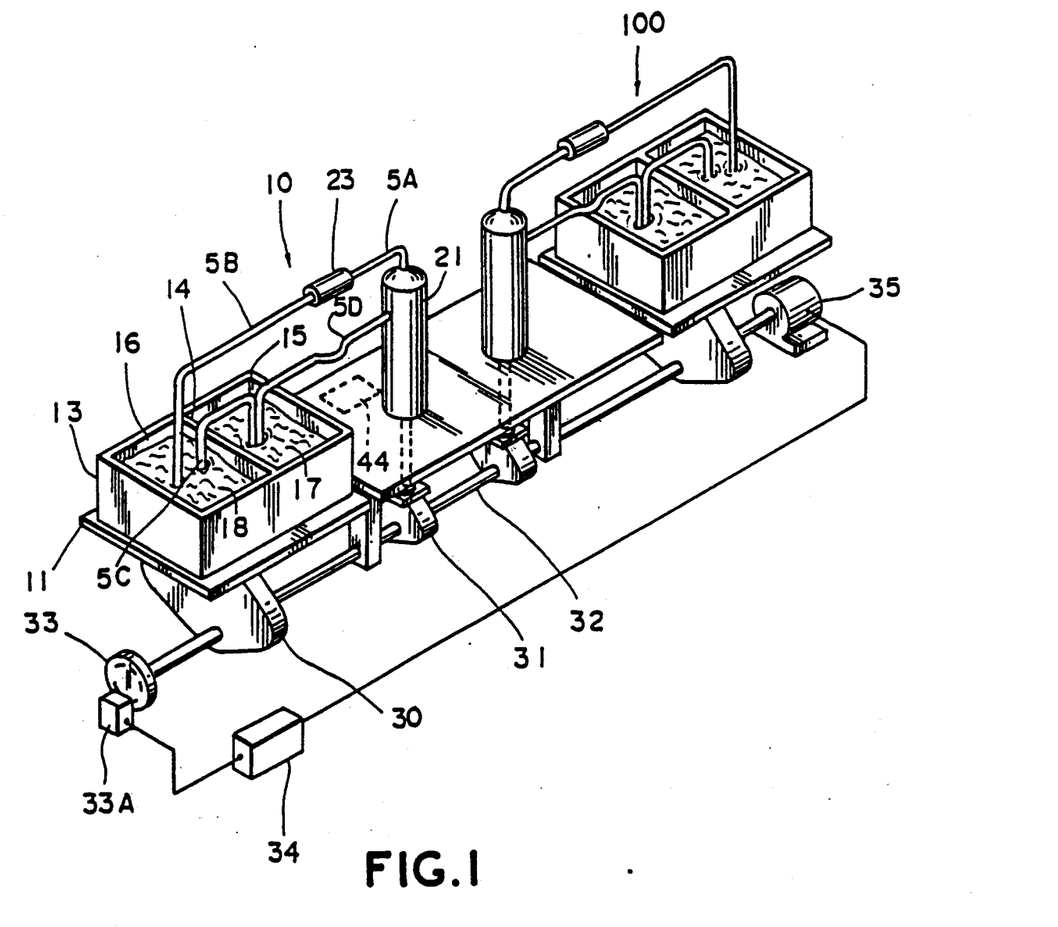
FIG. 1 is a front view of one embodiment of an analytical instrument in accordance with the present invention.
Figure 2A:
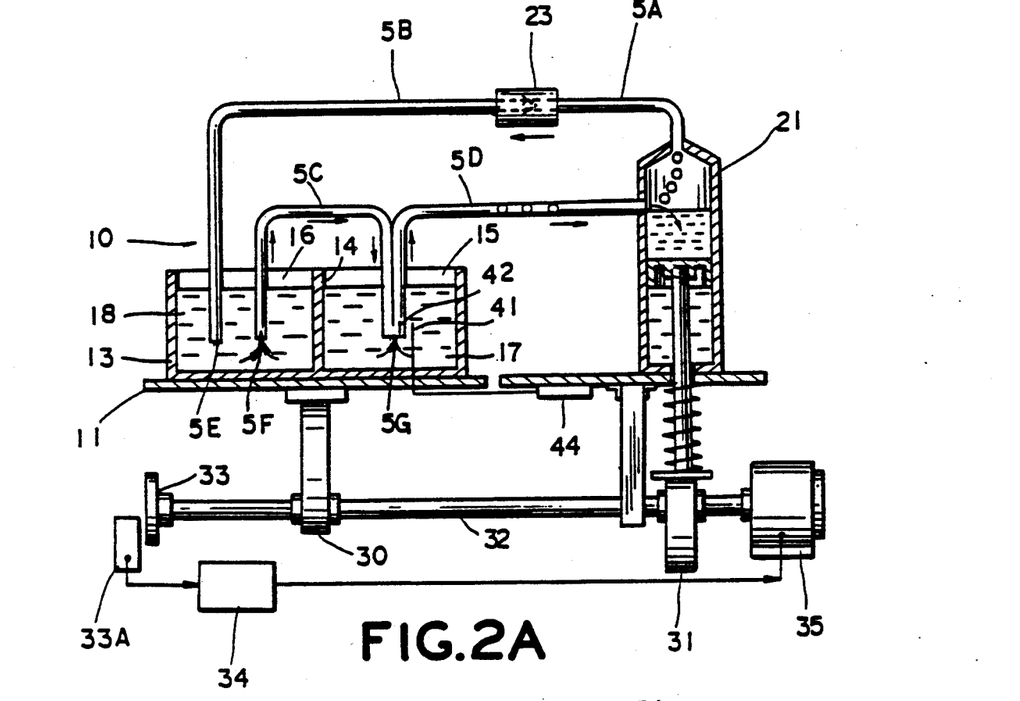
FIG. 2A-2C are front elevational views of a portion of the system shown in FIG. 1.
Figure 2B:
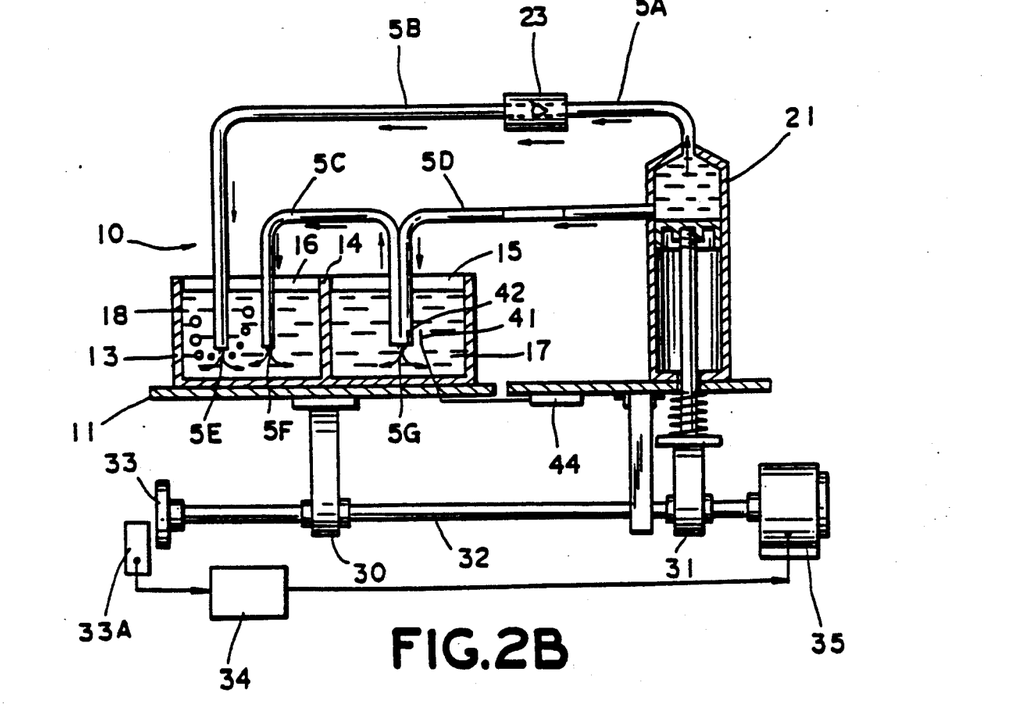
Figure 2C:
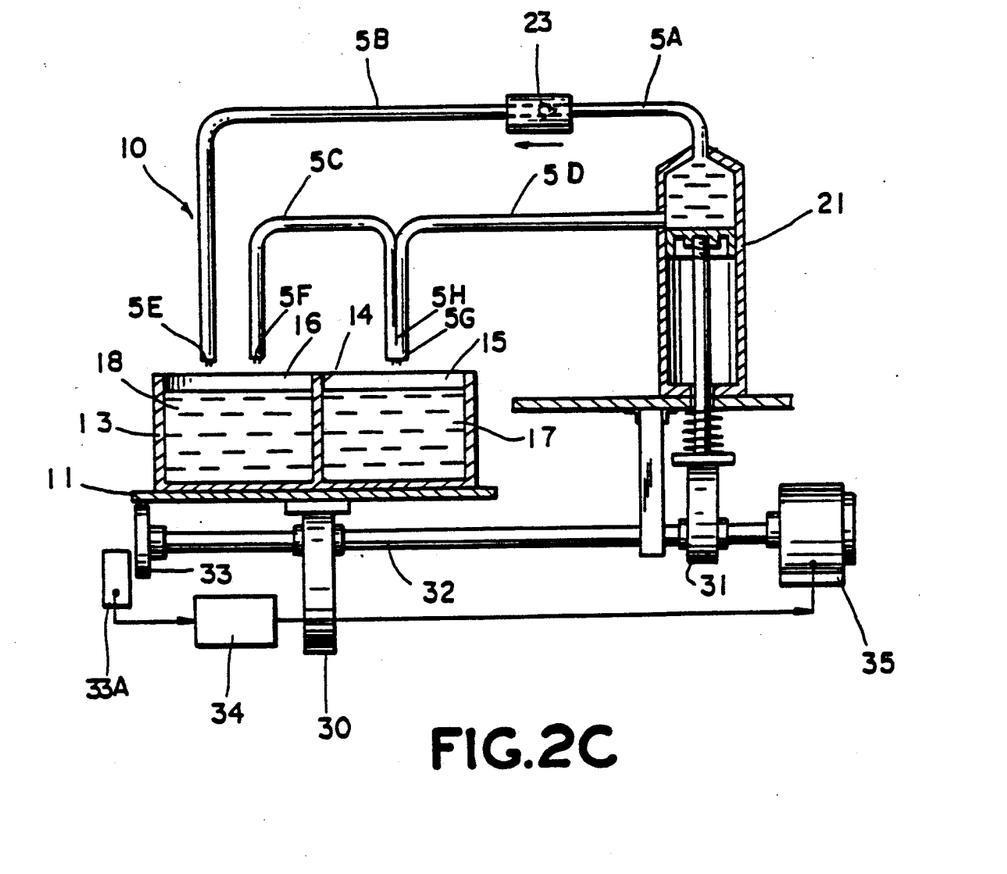

FIG. 1 shows an analytical instrument having multiple analyzing sub-stations 10 and 100, each being capable of performing particle analysis on a liquid sample. FIGS. 2A-2C are front views of the sub-station 10. Since the sub-stations are essentially the same, their operation will be described with reference only to sub-station 10 as shown in FIGS. 2A-2C.

Each sub-station represented by station 10 includes a platform 11 for holding a sample container 13 which is divided into two reservoirs 15 and 16 by dividing wall 14. Reservoir 15 holds a biological or industrial liquid suspension of particles to be analyzed and reservoir 16 holds a reagent 18. Depending on the type of analysis to be performed, the liquid sample 17 may be treated by the operator or other personnel before being added to reservoir 15.

A series of conduit members 5A-5D provide intimate liquid contact between reservoirs 15 and 16 and a piston pump 21. Member 5D provides liquid contact between sample reservoir 15 and pump 21. Check valve 23 is disposed between tube members 5A and 5B to permit liquid flow from the pump 21 to reservoir 16 while restricting flow in the opposite direction. Tube member 5C interconnects liquid sample reservoir 15 and reagent reservoir 16 to effect liquid flow therebetween as will be described in greater detail hereinbelow. It is to be understood that the liquid path created by conduit members 5A and 5B is optional. The system operates in accordance with the concepts of the underlying invention without the liquid pathway formed by conduit members 5A and 5B and those skilled in the art will appreciate from the discussion below that they are included for the purpose of increasing the system flow capacity and thus the efficiency of the flow system.

Figure 7A:
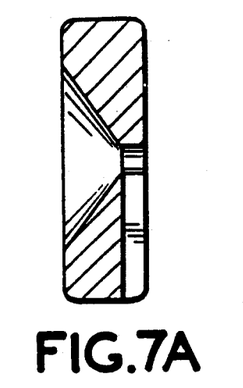
FIGS. 7A and 7B are enlarged side views of the apertures shown in FIGS. 2A-2C and 4A-4B.
Figure 7B:
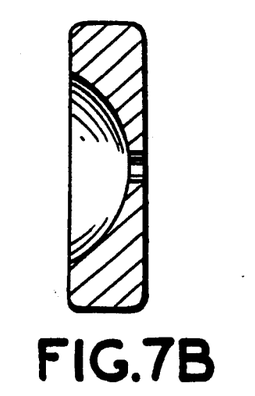

The ends of members 5B, 5C and 5D are provided, respectively, with aperture members 5E, 5F and 5G, termed the waste, fill and count apertures in view of their functions within the liquid flow system. In a typical blood cell count analysis, the liquid sample is aspirated through the count aperture 5G which has a sensing mechanism associated with it for detecting and counting each passing cell. The waste aperture 5E and fill aperture 5F are approximately 200 micrometers in diameter, while the diameter of count aperture 5G varies between 45 micrometers for counting red blood cells and 100 micrometers for white cell counting. The diameter of the count aperture corresponds to the diameter of the cell type being counted, thus allowing only one cell to pass through the aperture at a time. Preferably, the waste and fill aperture have a tapered, conical shape as shown in FIG. 7A, while the count aperture is arcuately shaped as shown in FIG. 7B.

Figure 4A:
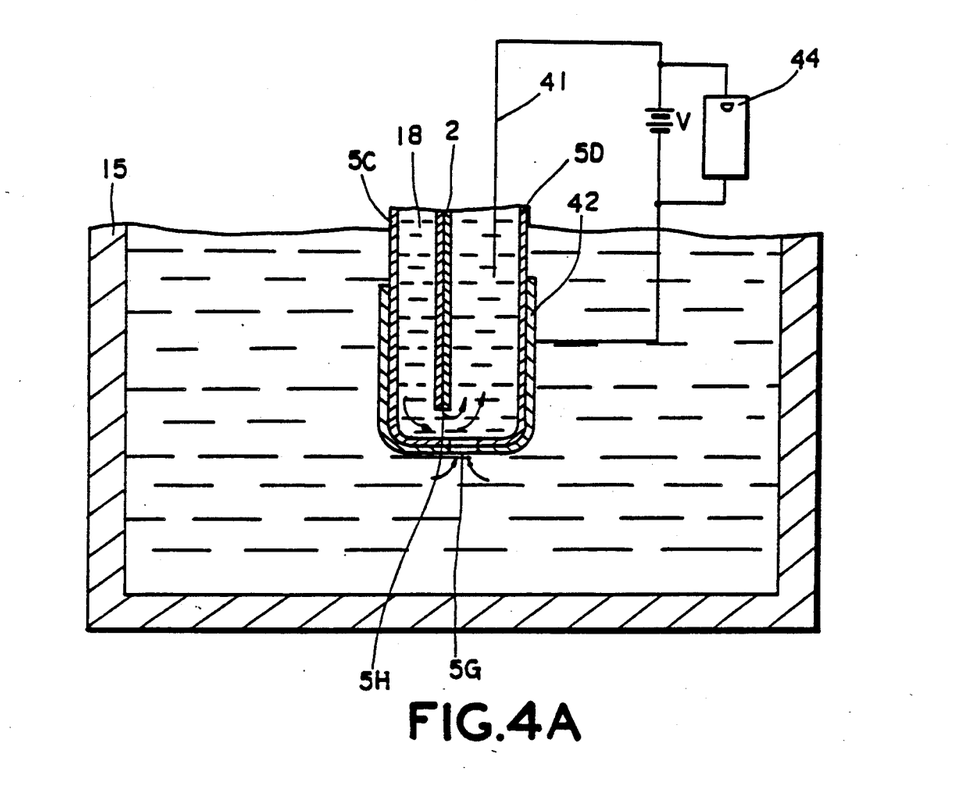
FIG. 4A is an enlarged view of the metered aperture area of FIGS. 2A-2C.
Figure 4B:
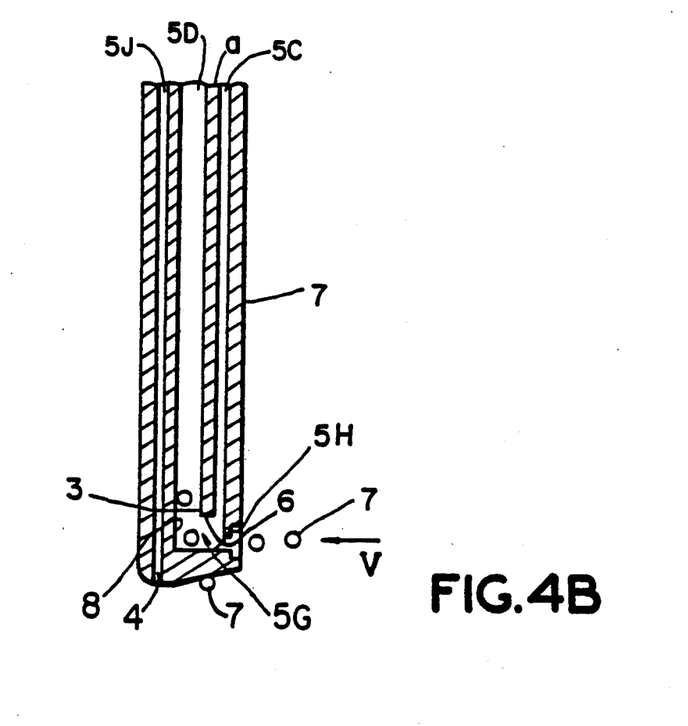
FIG. 4B is a further enlarged side view of the aperture.

During the counting phase of the analytical cycle, liquid is aspirated through fill aperture 5F from the diluent reservoir as a result of the negative pressure produced by downward movement of the piston in pump 21, and supplied through member 5C and around joining wall 2 where it contacts the sample liquid and suspended particles aspirated through aperture 5G at a point 5H just above count aperture 5G, as shown in FIGS. 4A and 4B.

As shown in FIG. 4B, the wall 2 adjoining members 5C and 5D terminates at a point 3 which is a greater distance above the aperture opening 5G than a point 6 at which outer wall 7 of member 5C terminates. This structure results in a dynamic operation whereby particles 7, which enter aperture 5G with a velocity V, are entrained by the liquid flowing in member 5C in an area of increased volume. As a result, particles 7 are less likely to collide with and become lodged against wall portion 8.

The bottom surface of aperture member 5G is tapered and elbowed at its rear portion where a passageway 4 is formed. The passageway 4 mates with a conduit member 5J and together they form a chamber through which air is forced. This forced air serves two purposes. First, when the aperture 5G is immersed in the liquid before the count portion of the analytical cycle, the air mixes the solution to create a uniform particle suspension in the reservoir. The mixing process is discontinued during the counting cycle. Second, when the aperture 5G is removed from the reservoir 15, drops that collect on the bottom surface of the aperture will be urged toward the passageway 4 by the inclined surface to a point where the forced air will blow them off the surface.

No liquid is aspirated through waste aperture 5E during the count phase because of the action of check valve 23. When the counting phase is complete, however, liquid flow is reversed by an upward movement of the piston in pump 21 and liquid exits from members 5A and 5B through aperture 5E as well as from members 5C and 5D through apertures 5F and 5G, respectively. When employed in the analytical instrument of the present invention, apertures 5E, 5F and 5G are all kept at the same level.

The operation of a typical working cycle of the analytical instrument will now be described with reference to FIGS. 2A-2C.

The mechanical movement of the platform 11 and piston pump 21 is coordinated by a novel cam system including a series of cams 30, 31 mounted on a common cam shaft 32. This system is described in detail in a contemporaneously filed U.S. patent application. The rotation of the shaft 32 causes the cams 30 and 31 to move the pump and platform at the proper time in the analytical cycle by virtue of the cam-followers and springs which, in tandem, act to translate the rotational motion of the cams to linear motion for displacement of the platform and pump. An encoder 33 and corresponding sensor 33A detect the relative rotational position of the shaft 32 and relay this information to a controller 34 for interpretation. Based on the relative position information, the controller outputs a stop, start or reverse control signal to motor 35. Wile this cam system is novel, it is not essential to the present invention and those of ordinary skill in the art will appreciate that the description thereof is provided for completeness and also that any method of coordinating and operating the platform and pump could be used in conjunction with the principles disclosed herein.

Figure 3A:
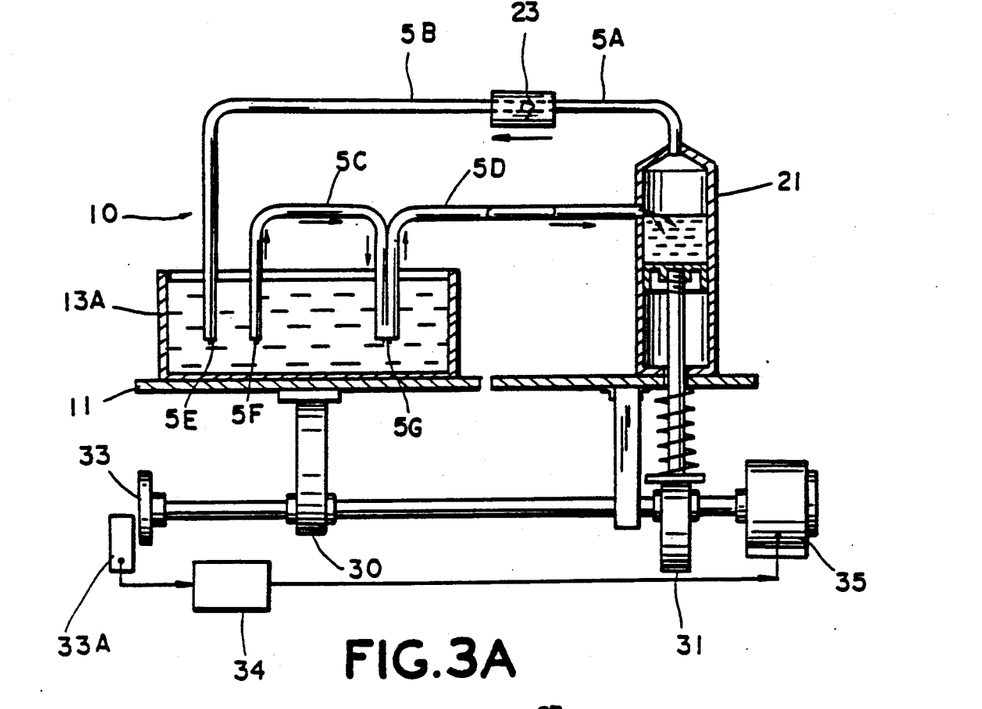
FIGS. 3A and 3B are front elevational views of the system of FIG. 1 at the time of first use.
Figure 3B:
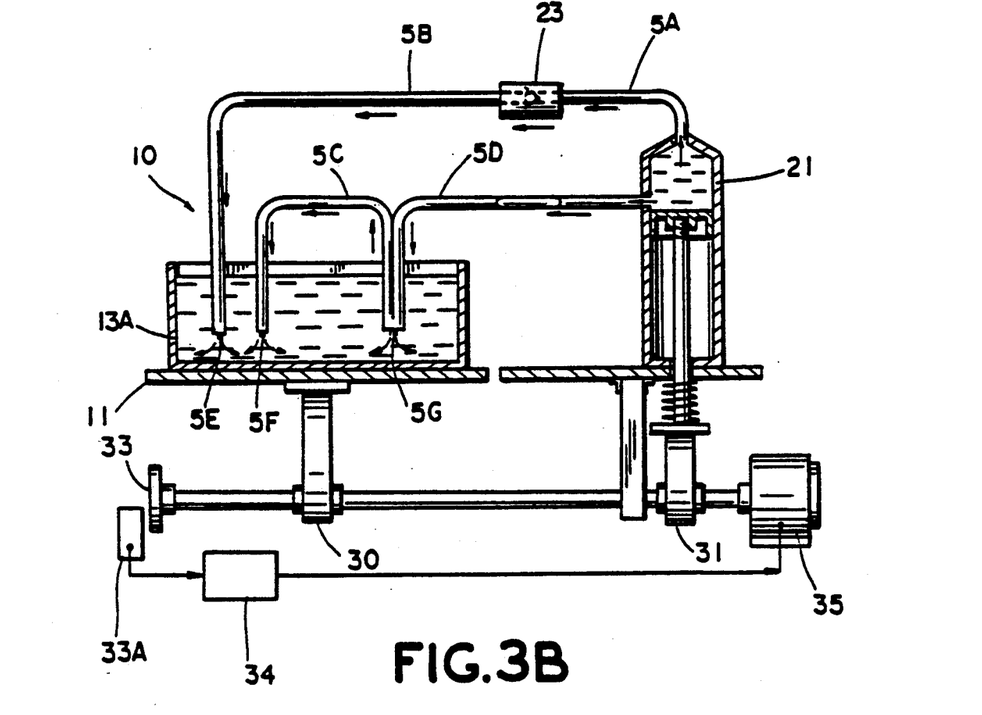

Before its first use, the liquid flow system shown in FIGS. 2A-2C is filled with air. Referring to FIG. 3A, an operator will initially prime the system with a liquid by using a container 13A similar to container 13 but without the dividing wall 14. When initiated, the cam system lifts the platform to immerse the apertures 5E, 5F and 5G in the liquid in container 13A. The negative pressure created by downward movement of the piston in pump 21 draws liquid into embers 5C and 5D through both the fill and count apertures. Despite the vacuum, no liquid is drawn into members 5A and 5B because of the action of check valve 23. As shown in FIG. 3B, at the end of the filling operation, the pump piston is caused to move upward, thereby forcing liquid back to the container 13A through tube members 5C, and 5D and through members 5A and 5B through check valve 23. At the end of the upper movement of the piston, tube members 5A, 5B, 5C and 5D are all filled with liquid.

Once primed, the system is ready for liquid sample analysis. After being lowered and removed, the container 13A is replaced by a liquid sample container 13. At this point, the anti-siphon feature of the present invention can be seen. Since the openings are all maintained at the same level, the liquid remaining in the tube members does not drain through apertures 5E, 5F and 5G when the sample containers 13A and 13 are interchanged. The surface tension between the liquid and the side and bottom walls of the tube adjacent the aperture also contribute to this effect.

Referring again to FIGS. 2A-2C, once the liquid sample container 13 has been situated, the cam system initiates an analytical cycle of the instrument. Again the piston moves downward within the pump 21 to create a negative relative pressure within the tube members causing liquid from the liquid sample 17 to be drawn up through the count aperture 5G, as indicted by the arrows in FIG. 2A. The count aperture size is chosen as indicated above such that one blood cell can pass through it at a time. A voltage potential U applied between a resistive wire electrode 41 placed in member 5C and plate electrode 42 disposed in sample reservoir 15 causes a current to flow through conducting liquid 17. Appropriate electronics 44 detect the change in current that occurs when a cell passes through the orifice of the aperture member 5G. Each passing cell causes the electronically recorded cell count to increase. The rate at which the piston descends is predetermined in accordance with the size of the aperture to establish a desired liquid flow rate through aperture 5G during the intake phase of the instrument cycle.

At the same time, liquid 18 is drawn into conduit member 5C from the reagent reservoir 16 through fill aperture 5F. Referring to FIGS. 4A and 4B, the reagent liquid 18 drawn into member 5C through fill aperture 5F travels along conduit member 5C to a point 5H behind count aperture 5G, where members 5C and 5D are in intimate liquid contact. Some blood cells which enter count aperture 5G will have a tendency to remain at the point 5H just behind the aperture, thus causing interruption of current flow and a false cell count. While the electrical characteristics of these false indications may be recognized and filtered out by appropriate circuitry, in the present system they are eliminated because the flow of reagent liquid 18 at the point of increased volume 5H entrains the lingering cells into the liquid flowing through member 5D, thereby flushing out the area just behind the aperture.

A bubble chamber 20 is formed at the top of the pump cavity for capturing bubbles formed in the liquid flow system. These bubbles are most commonly caused by the build-up of gas particles produced in the electrochemical reaction at the count aperture electrodes 41 and 42. These gaseous bubbles travel up through member 5D and are collected in the cycle is terminated and the action of the piston in pump 21 reversed, the liquid and bubbles collected in the piston cavity are caused to exit through the conduit members 5A and 5D, the system being designed so that the volume of liquid collected in the pump is greater than the combined volume of the three tube members. The collected bubbles and liquid are forced through check valve 23 and back into the reagent reservoir 16 through waste aperture 5E, while some of the liquid instead finds its way back into conduit 5C and exits through fill aperture 5F.

Since the liquid collected in the piston cavity during the count cycle exits through apertures 5E, 5F and 5G and is collected only through apertures 5F and 5G, if the flow rate created by pump 2 were the same during the fill and flush phases of the analytical cycle, the pressure across the apertures during each phase would not be the same.

To maintain the pressures across the apertures, it is necessary to increase by twofold the flow rate created by piston pump 21 during the flush portion of the analytical cycle as compared to that created during the fill or count portion. Increasing the flow velocity during the flush portion of the analytical cycle applies a pressure equal in magnitude to, but opposite in polarity to, the pressure during the fill phase. This helps to clear the apertures of any debris. Preferably, the pressure at the count aperture is maintained at six inches of mercury during both phases of liquid flow and the cross-sectional area of the waste aperture 5E is designed to be equal to the sum of the cross-sectional areas of the fill and count apertures 5F and 5G. For red blood cell counting, the fill, count and waste apertures typically have diameters of 200, 45, and 205 micrometers in diameter, respectively. For white cell counting the diameters are typically 200, 100 and 224 micrometers, respectively.

Once the analytical cycle is complete, the platform 11 is lowered as shown in FIG. 2C so that container 13 can be removed and replaced.

Thus, the present system is self-filling, being pumped by a cycle identical to that used for the analytical step. In addition, by maintaining the openings of the various tube members at the same level, the system avoids any possible inaccuracies or contamination that might otherwise be introduced by uncontrolled siphoning of liquid.

Figure 5:
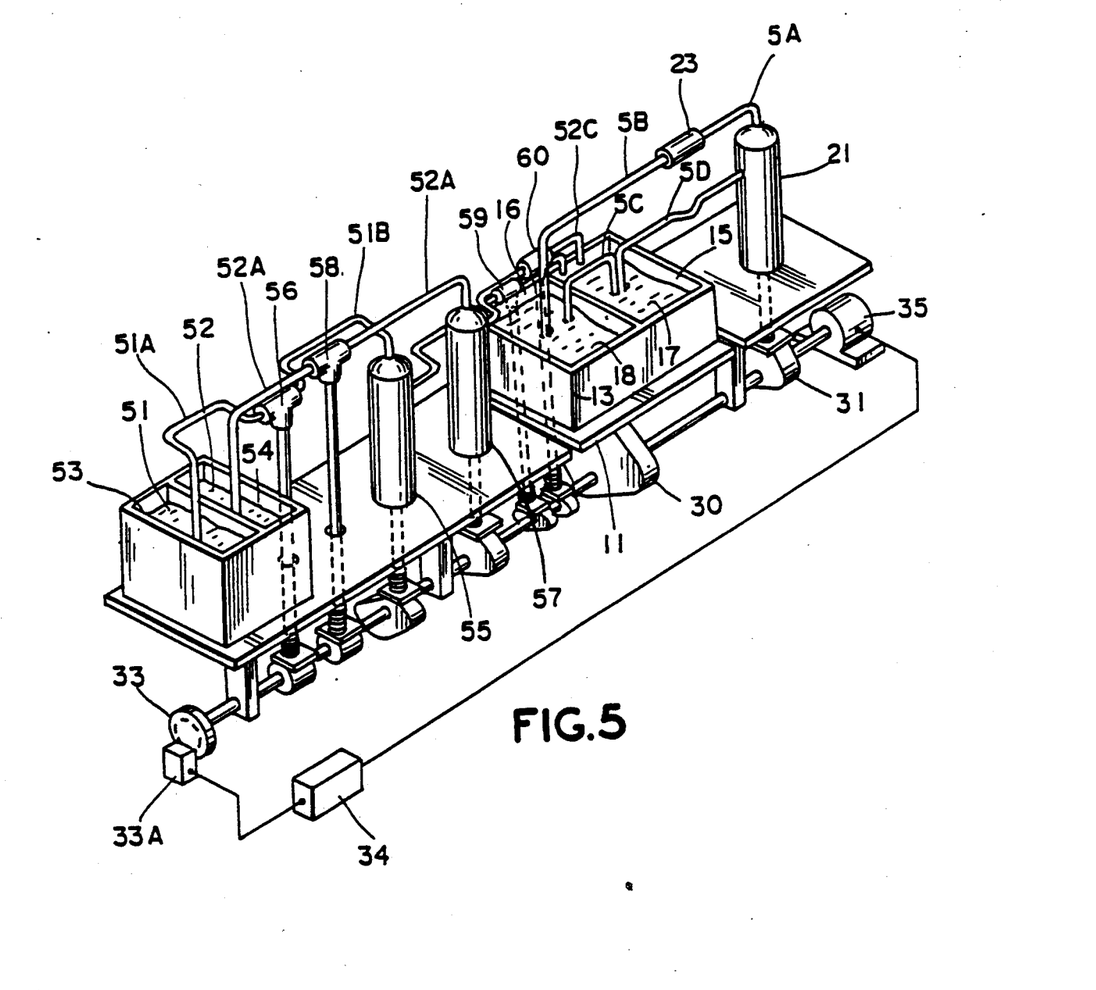
FIG. 5 is a plan view of a modification of the embodiment shown in FIG. 1.
Figure 6:
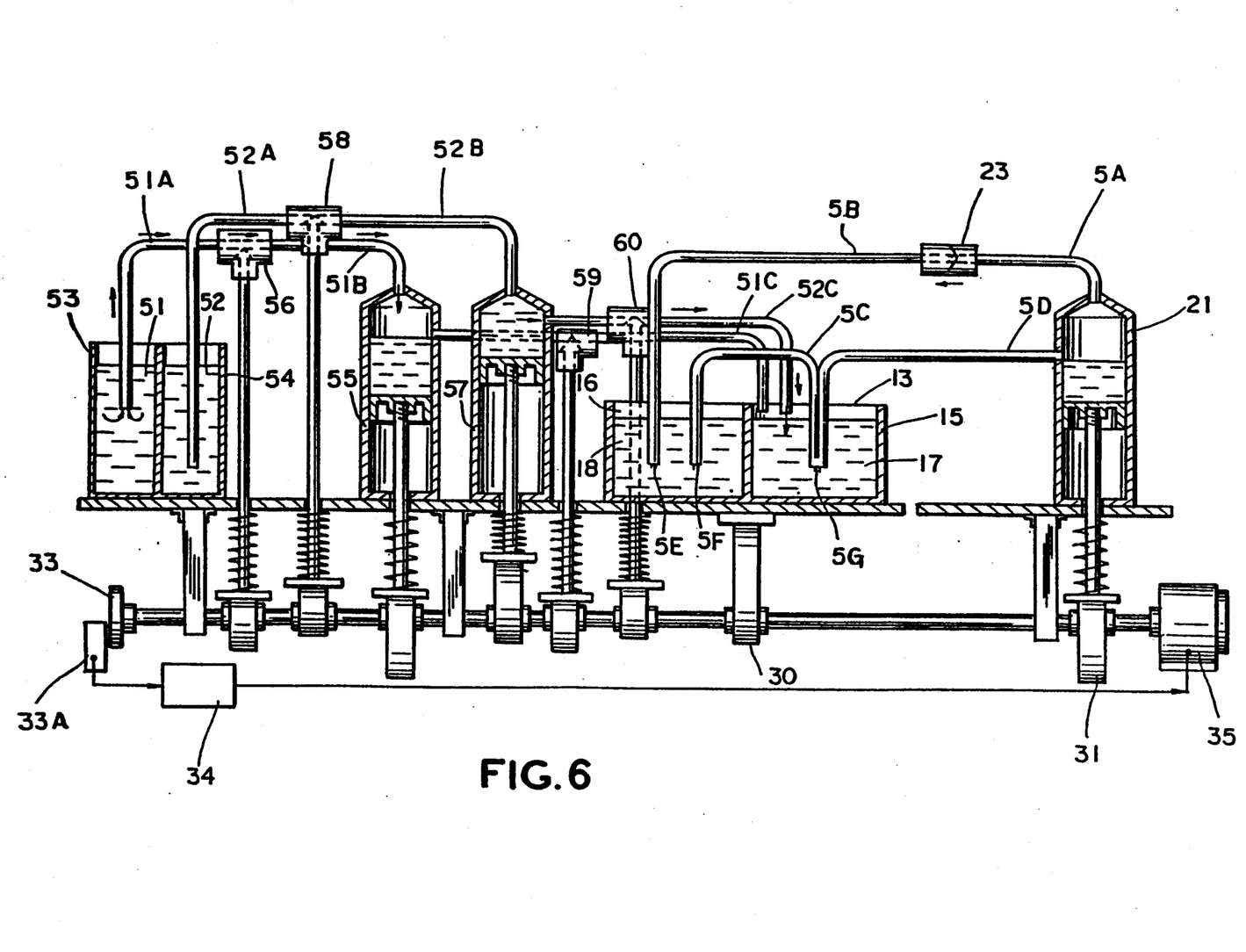
FIG. 6 is a front elevational view of the system shown in FIG. 5.

FIGS. 5 and 6 show another embodiment of the invention wherein additional liquids 51 and 52, contained in reservoirs 53 and 54 must be introduced into the liquid sample reservoir 15. These liquids may be additional liquid samples or other reagents and may be added during or before the actual counting step. Conduit members 51A and 51B provide liquid contact between additional piston pump 55 and reservoir 53 through valve 56, while members 52A and 52B define a liquid path from reservoir 54 to piston pump 57 through valve 58. Conduit members 51C and 52C define, respectively, liquid paths from the pumps 55 and 57 to the liquid sample reservoir 15 through valves 59 and 60.

If liquid 51 must be introduced into reservoir 15, the common shaft cam system would be designed to operate the elements 55, 56 and 59 at the appropriate time in the instrument cycle. First, valve 59 would be closed and valve 56 opened. The piston pump 55 would then aspirate liquid 51 from the reservoir 53 up along member 51A, through valve 56 and into the piston cavity of pump 55 as shown in FIG. 6. After the appropriate amount of liquid 51 was collected in the cavity, valve 56 would be closed and valve 59 opened. The action of piston pump 55 would then be reversed to pump liquid into reservoir 15 through member 51C. This portion of the cycle is shown in FIG. 6 by the combination of valves 58 and 60 with pump 57.

In order to preserve the anti-siphon feature of the system, the open output ends of conduit members 51C and 52C in reservoir 15C should be kept at the same level as the open input ends of members 51A and 52A, respectively, and after completion of the count cycle, valves 56, 58, 59 and 60 should be maintained in the open position.

Referring again to FIG. 1, the operation of the additional analyzing sub-stations is essentially the same as described hereinabove, with the exception of some system timing concerns. In order to reduce the load demand on the motor and thereby decrease the amount of electrical noise introduced into the counting system, the cams are designed so that the piston pump in each sub-station will sequentially effect the counting phase of the cycle before any discharge of liquid, i.e., the pump in station 10 will aspirate liquid through its count aperture to effect a cell count and then the pump in station 100 will draw liquid through its corresponding count aperture before the pump in station 10 begins to output the liquid drawn into its cavity. Once all of the sub-stations have performed their counts, the pumps are forced by the cam system to simultaneously initiate the output phase. Another advantage to this arrangement is that the system only requires one set of counting electronics with a counting signal input switchable between each sub-station of the measurement cycle, since noise created by the operation of the motor is not a concern during the flush portion of the analysis.

The detailed description of the preferred embodiment having been set forth herein, it is to be understood that there can be deviation and modification without departing from the true scope and essence of the disclosed invention.

We claim:

1. A liquid flow system for use with analytical instruments comprising:
   a reagent reservoir for holding a quantity of a reagent;
   a sample reservoir for holding a quantity of a liquid suspension of particles to be analyzed;
   a pumping reservoir;
   first conduit means having an upstream end capable of being selectively extended into the reagent reservoir below the normal level of reagent and a downstream end capable of being selectively extended into the sample reservoir below the normal level of liquid in the sample reservoir;
   second conduit means having an upstream end capable of being selectively extended into the sample reservoir below the normal level of liquid, said upstream end having an aperture being sized to permit the passage of individual suspended particles from the sample reservoir into the second conduit means, and a downstream end extending into the pumping reservoir;
   the upstream and downstream ends of the first conduit means and the apertured upstream end of the second conduit being at the same level;
   the downstream end of the first conduit means being in fluid communication with the upstream apertured end of the second conduit means so that reagent liquid from the first conduit means is released into the second conduit means through a common passageway located just upstream of the particle-sized aperture and entrains the particles as they enter the second conduit means through the aperture;
   first electrode means located in the sample reservoir;
   second electrode means located in the second conduit means downstream from the aperture; and
   pumping means for drawing reagent through the first conduit means into the second conduit means and for drawing reagent and entrained sample liquid and particles through the second conduit means past the means and into the pumping reservoir.

2. The system of claim 1 further comprising:
   third conduit means having a downstream end capable of being selectively extended into the reagent reservoir for connecting the upper portion of the pumping reservoir and the reagent reservoir and including valve means for permitting flow only from the pumping reservoir to the reagent reservoir, the downstream end of the third conduit means being maintained at the same level as the upstream and downstream ends of the first conduit means and the apertured upstream end of the second conduit means, wherein the pumping means forces reagent and entrained sample liquid and particles collected in the pumping reservoir back through the second conduit means and, having been forced back through the second conduit means, then back through the first conduit means and also forces reagent and entrained sample liquid and particles collected in the pumping means through the third conduit means.

3. The system of claim 2 wherein the pumping reservoir further comprises a bubble chamber formed at a top end thereof for capturing bubbles flowing in the second conduit means when the pump means draws reagent and entrained sample liquid and particles through the second conduit means and for releasing the captured bubbles through the third conduit means and the valve means into the reagent reservoir.

4. The system of claims 1, 2 or 3 wherein a downstream portion of the first conduit means is formed in a unitary manner with an upstream portion of the second conduit means such that reagent drawn into the first conduit means and flowing into the second conduit means entrains the particles drawn into the apertured end of the second conduit means at an area of increased cross-sectional area relative to that of the downstream portion of the second conduit means through which the entraining reagent liquid flows.

5. The system of claim 4 wherein the first conduit means is of a generally inverted U-shape.

6. The system of claim 5 wherein the unitarily formed downstream portion of the first conduit means and the upstream portion of the second conduit means are formed in a single unit which includes a passageway for forced air formed at a rear portion of the unit, the bottom surface of the unit being elbowed at a rear portion and tapered from the rear to a front position where the metered aperture of the second conduit means is disposed such that any drops of liquid collecting on the bottom surface of the unit are urged toward the forced air passageway, and the system further comprises means for forcing air through the forced air passageway.

7. The system of claim 6 wherein the upstream end of the first conduit means and the downstream end of the third conduit means are also provided with apertures chosen such that the cross-sectional area of the aperture of the third conduit means is equal to the sum of the cross-sectional areas of the apertures in each of the first and second conduit means.

8. The system of claim 7 wherein the aperture in the second conduit means is approximately forty-five micrometers in diameter and the aperture in the first conduit means is approximately two hundred micrometers in diameter.

9. The system of claim 7 wherein the aperture in the second conduit means is approximately on hundred micrometers in diameter and the aperture in the first conduit means is approximately two hundred micrometers in diameter.

10. The system of claim 7 wherein said pump means is a piston pump having the third reservoir formed therein.

11. The system in accordance with claim 10 wherein the valve means is a check valve.

12. The system in accordance with claim 11 wherein the conduit means is a series of flexible tubes.

13. An analytical instrument for analyzing biological or industrial liquid samples comprising:
    a plurality of analyzing sub-stations, each sub-station comprising:
    a reagent reservoir for holding a quantity of a liquid reagent;
    a sample reservoir for holding a quantity of a liquid suspension of particles to be analyzed, the particles having a different value of an electrical characteristic than the value of the same characteristic of the reagent;

a pumping reservoir;

first conduit means having an upstream end capable of being selectively extended into the reagent reservoir below the normal level of reagent and a downstream end capable of being selectively extended into the sample reservoir below the normal level of liquid in the sample reservoir;

second conduit means having an apertured upstream end capable of being selectively extended into the sample reservoir below the normal level of liquid, the aperture being sized to permit the passage of individual suspended particles from the sample reservoir into the second conduit means, and a downstream end extending into the pumping reservoir;

the upstream and downstream ends of the first conduit means and the apertured upstream end of the second conduit means being at the same level;

the downstream end of the first conduit means being in fluid communication with the upstream apertured end of the second conduit means so that reagent liquid from the first conduit means is released into the second conduit means just upstream of the particle-sized aperture and entrains the particles as they enter the second conduit means through the aperture;

first electrode means located in the sample reservoir;

second electrode means located in the second conduit means downstream from the aperture; and pumping means for drawing reagent through the first conduit means into the second conduit means, for drawing reagent and entrained sample liquid and particles through the second conduit means past the second electrode means and into the pumping reservoir;

means for applying a potential between the first and second electrodes such that a current flows therebetween;

means for detecting a change in the current when an individual suspended particle passes through the apertured end of the second conduit means; and counting means responsive to the detection means for counting the number of particles passing through the aperture of the second conduit means, said means for applying a potential, said counting means and said detecting means all being capable of being switched to each of the sub-stations;

said analytical instrument further comprising:

means for coordinating the pumping means and the selective exposure of the apertures; and means responsive to the coordinating means for mechanically effecting the operation of the pumping means and the selective exposure of the apertures.

14. The analytical instrument of claim 13 wherein each sub-station further comprises third conduit means having a downstream end capable of being selectively extended into the reagent reservoir for connecting the upper portion of the pumping reservoir and the reagent reservoir and including valve means for permitting flow only from the pumping reservoir to the reagent reservoir, the downstream end of the third conduit means being maintained at the same level as the upstream and downstream ends of the first conduit means and the apertured upstream end of the second conduit means, wherein the pumping means forces reagent and entrained sample liquid and particles collected in the pumping reservoir through the second conduit means and then back through the first conduit means through said passageway and also forces reagent and entrained sample liquid and particles collected in the pumping means through said third conduit means.

15. The analytical instrument of claim 14 wherein the pumping reservoir further comprises a bubble chamber formed at a top end thereof for capturing bubbles flowing in the second conduit means when the pump means draws reagent and entrained sample liquid and particles through the second conduit means and for releasing the captured bubbles through the third conduit means and the valve means into the reagent reservoir.

16. The instrument of claims 13, 14 or 15 wherein a downstream portion of the first conduit means is formed in a unitary manner with an upstream portion of the second conduit means such that reagent drawn into the first conduit means and flowing into the second conduit means entrains the particles drawn into the apertured end of the second conduit means at an area of increased cross-sectional area relative to that of the downstream portion of the second conduit means through which the entraining liquid flows.

17. The instrument of claim 16 wherein the first conduit means has a generally inverted U-shape.

18. The analytical instrument according to claim 17 wherein the upstream end of the first conduit means and the downstream end of the third conduit means are also provided with apertures chosen such that the cross-sectional area of the aperture in the first conduit means is equal to the sum of the cross-sectional areas of the apertures in each of the first and second conduit means.

19. The instrument of claim 18 wherein the aperture in the second conduit means is approximately forty-five micrometers in diameter and the aperture in the first conduit means is approximately two hundred micrometers in diameter.

20. The analytical instrument of claim 18 wherein the aperture in the second conduit means is approximately one hundred micrometers in diameter and the aperture in the third conduit means is approximately two hundred micrometers in diameter.

21. The analytical instrument of claim 18 wherein the pump means is a piston pump having the pumping reservoir formed therein.

22. The analytical instrument of claim 21 wherein the valve means is a check valve.

23. The analytical instrument of claim 22 wherein the conduit means is a series of flexible tubes.

24. The analytical instrument of claims 13 or 14 wherein said sub-station further comprises a plurality of additional reservoirs for holding, respectively, a plurality of additional reagents:

a plurality of pumps and corresponding additional conduit means each having an upstream end capable of being selectively extended into its corresponding additional reservoir and a downstream end capable of releasing liquid into the reagent reservoir for selectively pumping the reagents in said additional reservoirs along liquid paths to said reagent reservoir, the upstream and downstream ends of each additional conduit means being at the same level;

second valve means for selectively closing and opening the liquid paths from the additional reservoirs to the reagent reservoir; and the coordination means also coordinates the selective pumping of the additional reagents and the opening and closing of said second valve means.

25. The system of claim 6 wherein the air forcing means forces air through the air passageway to remove any drops urged toward the air passageway along the bottom surface of the unit when the conduit means are removed from the respective reservoirs.

26. The system of claim 6 wherein the air forcing means forces air through the air passageway into the sample reservoir to mix the reservoir contents so as to create a uniform particle suspension in the sample reservoir before the drawing action of the pumping means is effected.

* * * * *

UNITED STATES PATENT AND TRADEMARK OFFICE
CERTIFICATE OF CORRECTION

PATENT NO.   : 5,094,818
DATED        : March 10, 1992
INVENTOR(S)  : M. Longman, O. Proni, R.A. Burdman It is certified that error appears in the above-identified patent and that said Letters Patent is hereby corrected as shown below:

Column 4, line 38, delete "embers" and insert --members--.
Column 5, line 36, after "collected in the" insert --top of the pump cavity. As shown in FIG. 2B after the count--.
Column 5, line 37, after "21" insert --is--.
Column 8, line 49, delete "on" insert --one--.

Signed and Sealed this

Twenty-eighth Day of September, 1993

Attest:

BRUCE LEHMAN

*Attesting Officer*      *Commissioner of Patents and Trademarks*